United States Patent
Li et al.

(10) Patent No.: US 12,158,439 B1
(45) Date of Patent: Dec. 3, 2024

(54) DRAIN-GATE VOLTAGE EXCITATION AND SOURCE-DRAIN CURRENT ACQUISITION SYSTEM AND METHOD FOR GAS-SENSITIVE ORGANIC FIELD EFFECT TRANSISTORS

(71) Applicant: TianJin University, Tianjin (CN)

(72) Inventors: Shuang Li, Tianjin (CN); Jie Fu, Tianjin (CN); Dong Ming, Tianjin (CN)

(73) Assignee: TianJin University, Tianjin (CN)

( * ) Notice: Subject to any disclaimer, the term of this patent is extended or adjusted under 35 U.S.C. 154(b) by 0 days.

(21) Appl. No.: 18/755,562

(22) Filed: Jun. 26, 2024

(51) Int. Cl.
*G01N 27/12* (2006.01)
*G01N 27/414* (2006.01)
*G01N 33/00* (2006.01)
*H03K 17/687* (2006.01)

(52) U.S. Cl.
CPC ....... *G01N 27/122* (2013.01); *G01N 27/4141* (2013.01); *G01N 27/4148* (2013.01); *G01N 33/0027* (2013.01); *G01N 33/0031* (2013.01); *H03K 17/687* (2013.01)

(58) Field of Classification Search
CPC ............. G01N 27/122; G01N 27/4141; G01N 27/4148; G01N 33/0027; G01N 33/0031; H03K 17/687
See application file for complete search history.

(56) References Cited

U.S. PATENT DOCUMENTS

| | | | |
|---|---|---|---|
| 7,403,065 B1 | 7/2008 | Gresham et al. | |
| 2008/0012007 A1* | 1/2008 | Li | G01N 27/4145 438/49 |
| 2010/0019783 A1* | 1/2010 | Willard | G01N 27/414 702/65 |
| 2014/0235463 A1* | 8/2014 | Rothberg | G01N 27/4145 506/38 |

FOREIGN PATENT DOCUMENTS

| | | |
|---|---|---|
| CN | 104467700 A | 3/2015 |
| CN | 105758898 A | 7/2016 |
| CN | 107765067 A | 3/2018 |
| CN | 108761284 A | 11/2018 |

\* cited by examiner

*Primary Examiner* — Paul M. West

(57) ABSTRACT

The present disclosure provides a drain-gate voltage excitation and source-drain current acquisition system and method for gas-sensitive organic field effect transistors (OFETs). The system includes an acquisition device and a gas-sensitive OFET array. The device includes a microcontroller module, a power supply management module, a voltage excitation module, a voltage regulation module, a transimpedance amplifier (TIA) module, a fully-differential low-side current detection module, a voltage acquisition module, a signal transmission module and an array switching module. In the present disclosure, the real-time monitoring of various harmful gases and the performance testing of the gas-sensitive OFETs are realized. The device has two current detection modes, thereby not only stabilizing drain electric potentials, but also enabling drain-source currents to be measured with sufficient accuracy.

12 Claims, 3 Drawing Sheets

DRAIN-GATE VOLTAGE EXCITATION AND SOURCE-DRAIN CURRENT ACQUISITION SYSTEM AND METHOD FOR GAS-SENSITIVE ORGANIC FIELD EFFECT TRANSISTORS

CROSS-REFERENCE TO RELATED APPLICATIONS

This application claims priority of Chinese Patent Application No. 202310970676.2, filed on Aug. 3, 2023, the entire contents of which are incorporated herein by reference.

TECHNICAL FIELD

The present disclosure relates to the technical field of sensors, and more particularly, relates to a drain-gate voltage excitation and source-drain current acquisition system and method for gas-sensitive organic field effect transistors (OFETs).

BACKGROUND

Compared with the traditional biological gas sensing and monitoring technology, the gas sensing and monitoring based on an OFET has the functions of sensing and signal amplification, and has the advantages of high sensitivity, high selectivity and high stability. In addition, the gas sensing and monitoring based on OFET not only has the characteristics of breathability, anti-perspiration corrosion, and long-time wearing without falling off, but also has the features of simple manufacturing process, rapid response, low sample size, and wide detection range. To meet the requirements of flexible manufacturing for real-time, efficient and stable acquisition in special environment, the high sensitivity, high selectivity and high stability of the OFET array gas sensing are realized. Breaking through the bottleneck of sensing technology, the miniaturization of chip, continuous energy supply for a long time, accessibly non-inductive wearing, and the long-term efficient and stable monitoring of external harmful gases are realized, applying in the real-time alarm of harmful gases on disaster and accident sites, thereby improving the safety protection technology level in the field of disaster prevention and relief.

SUMMARY

To overcome the above defects in the prior art, examples of the present disclosure provide a drain-gate voltage excitation and source-drain current acquisition system and method for gas-sensitive OFETs. The system includes a gas-sensitive OFET array, a drain/gate voltage excitation and source-drain current acquisition device for gas-sensitive OFETs and a wireless terminal. Since different concentrations of different harmful gases act on the gas-sensitive OFETs, different response currents are produced. A weighted sum of two current detection methods is used to improve the accuracy and range of current detection, combined with the rapid switching technology of the gas-sensitive OFET array, to realize the real-time monitoring of various harmful gases.

In order to achieve the above object, the present disclosure provides the following technical solutions. A drain-gate voltage excitation and source-drain current acquisition system for gas-sensitive OFETs is provided, including an acquisition device and a gas-sensitive OFET array. The device includes a microcontroller module, a power supply management module, a voltage excitation module, a voltage regulation module, a transimpedance amplifier (TIA) module, a fully-differential low-side current detection module, a voltage acquisition module, a signal transmission module and an array switching module. Through the device, the excitation of drain voltages and gate voltages in the gas-sensitive OFETs and the acquisition of source-drain currents are realized, and the performance testing of the gas-sensitive OFETs and the long-term efficient and stable monitoring of external harmful gases are finally realized through data analysis. The specific design is as follows.

The microcontroller module is configured to realize the information interaction with the voltage excitation module, the voltage detection module and the signal transmission module and control the array switching module.

The voltage excitation module is configured to complete the independent excitation of gate and drain electrodes.

The voltage regulation module is configured to perform inverting and noninverting double gain amplification and following on voltages directly outputted by the voltage excitation module, and output the voltages to the gate and drain electrodes, ensuring that excitation voltages on two electrodes range from $-5$ V to $0$ V, output currents being in mA level, and preventing the mismatching of output currents caused by different performance of the gas-sensitive OFETs.

The TIA module is configured to include a JFET-type single channel operational amplifier ADA4622 and have a bias current in pA level, reducing a baseline current to a maximum extent; and a 1 MΩ precision resistor with a precision of 0.1% is used for a feedback resistor in the module.

The fully-differential low-side current detection module is configured to construct a one-stage fully-differential amplification circuit with a gain of 10 using an LT6370 instrumentation amplifier, and construct a two-stage amplification circuit with a gain of 500 using OPA4134, a total gain being 5000.

The voltage acquisition module, constructed by using a 16-bit ADS1115 chip, is configured to have four input channels for detecting a gate voltage, a drain voltage, an output voltage of the TIA module and an output voltage of the fully-differential low-side current detection module to realize the closed-loop control of the gate and drain voltages and simultaneously detect output voltages of two current detection modules.

The signal transmission module, using an ESP32 chip, is configured to switch Bluetooth low energy (BLE) and local area network (LAN) at any time to adapt to the wireless data transmission in various environments.

The array switching module is configured to use ADG series analog switches with low conduction internal resistance, the switch being capable of switching one of multiple inputs to a common output, to realize the fast switching scanning of the array.

The gas-sensitive OFET array is set for detecting five external harmful gases of carbon dioxide, sulfur dioxide, nitrogen dioxide, carbon monoxide and ammonia, with a size of 5*5; each row in the array detects one gas; the array shares a source electrode; and each row of the array shares a grid electrode and a drain electrode. Therefore, a total of 11 electrodes cooperate, including 5 drain electrodes D1\D2\D3\D4\D5, 5 grid electrodes G1\G2\G3\G4\G5 and one source electrode S. The array switching module can realize the rapid switching among rows of the array. Moreover, since there are two current detection circuits, the total gate leakage current caused by a common source and common grids can be filtered out from drain-source currents.

In a preferred implementation, in the microcontroller module, an STM32F103C8T6 chip is adopted, functioning through serial peripheral interface (SPI) communication, inter-integrated circuit (IIC) communication, serial communication and level output of input/output (IO) port of the chip; and in the power supply management module, a TPS7A5301 chip is adopted to realize the conversion from 3.7 V input to 3.3 V output of a lithium battery, providing a stable and suitable working voltage for the microcontroller module, the signal transmission module and the array switching module; an LTC3245 chip is adopted to realize an output of a lithium battery from 3.7 V up to 5 V, supplying power for the voltage excitation module, the voltage acquisition module and the TIA module, and providing positive power supply support for the voltage regulation module and the fully-differential low-side current detection module; and an LTC1983 chip is adopted to realize an output from 5 V to −5 V, providing negative power supply support for the voltage regulation module and the fully-differential low-side current detection module.

In a preferred implementation, in the voltage excitation module, a 16-bit DAC8562 chip is adopted; and one of double channels of output voltages is outputted to the gate electrode via the voltage regulation module, and the other of the double channels of output voltages is outputted to the drain electrode via the voltage regulation module; and the voltage regulation module is constructed from a 6-channel amplifier including a four-channel precision operational amplifier AD8674 and a two-channel precision operational amplifier AD8672.

The present disclosure further includes a fully-differential low-side current detection method. A current is converted to a voltage using a precision sampling resistor, a voltage drop of the precision sampling resistor is amplified using an LT6370 instrumentation amplifier, and a feedback loop is constructed by using the characteristic of a very high input impedance of an operational amplifier, so that drain-source currents of gas-sensitive OFETs pass through the precision sampling resistor to form a voltage negative feedback circuit without drawing currents from the gas-sensitive OFETs, thereby not only stabilizing drain electric potentials and enabling the drain electric potentials to be well controlled, but also enabling the drain-source currents to be measured with sufficient accuracy. The method requires attention to that: the precision sampling resistor is equivalent to the output resistance of the operational amplifier in the circuit. According to the criterion that the output impedance of a previous stage circuit is to be smaller, the value of the precision sampling resistor is not to be too large. However, since it is not sensitive to a change response of a current when a resistance value is too small, a precision resistor with a resistance value of 100Ω is selected and needs to be calibrated before use.

The present disclosure further includes a method for implementing detection of different orders of currents with higher accuracy using a weighted mode, including the steps of: adopting two current detection methods, namely TIA and fully-differential low-side current detection; taking a weighted sum of results of currents acquired by the two methods as a final result of a current transmitted to a terminal; and adding different weights to the two current detection results according to different orders of drain-source currents, followed by summing.

The present disclosure further includes a wireless terminal for drain/gate voltage excitation and source-drain current acquisition for gas-sensitive OFETs for implementing the control of a drain-gate voltage excitation and source-drain current acquisition device for gas-sensitive OFETs, and the wireless transmission, storage and intelligent analysis of detection data through a system wireless terminal by connecting a wireless fidelity (Wi-Fi) signal or a BLE signal sent by a signal transmission module and using three communication modes, data coding at a signal sending end and data parsing at the wireless terminal, to realize the sensitive analysis and timely alarm of various harmful gases.

The technical effects and advantages of the present disclosure are as follows.

The present disclosure provides a method for implementing detection of different orders of currents with the same accuracy using a weighted mode, including the steps of: adopting two current detection methods, namely TIA and fully-differential low-side current detection; taking a weighted sum of results of currents acquired by the two methods as a final result of a current transmitted to a terminal; and adding different weights to the two current detection results according to different orders of drain-source currents, followed by summing. In the present disclosure, the measurement accuracy of the drain-source currents is improved, and the overflow of the TIA circuit due to excessive currents is effectively prevented. The method provides a systematic and scientific solution for drain-source current detection.

In the present disclosure, through the device, the real-time monitoring of various harmful gases and the performance testing of the gas-sensitive OFETs are realized. The device has two current detection modes, a feedback loop is constructed by using the characteristic of a very high input impedance of the operational amplifier, so that the drain-source currents of the gas-sensitive OFETs pass through the precision sampling resistor to form the voltage negative feedback circuit without drawing currents from the gas-sensitive OFETs, thereby not only stabilizing drain electric potentials and enabling the drain electric potentials to be well controlled, but also enabling the drain-source currents to be measured with sufficient accuracy. Moreover, the device has the advantages of miniaturization, multi-parameter measurement and real-time analysis, and has very important market application potential.

DETAILED DESCRIPTION

Figure 1:
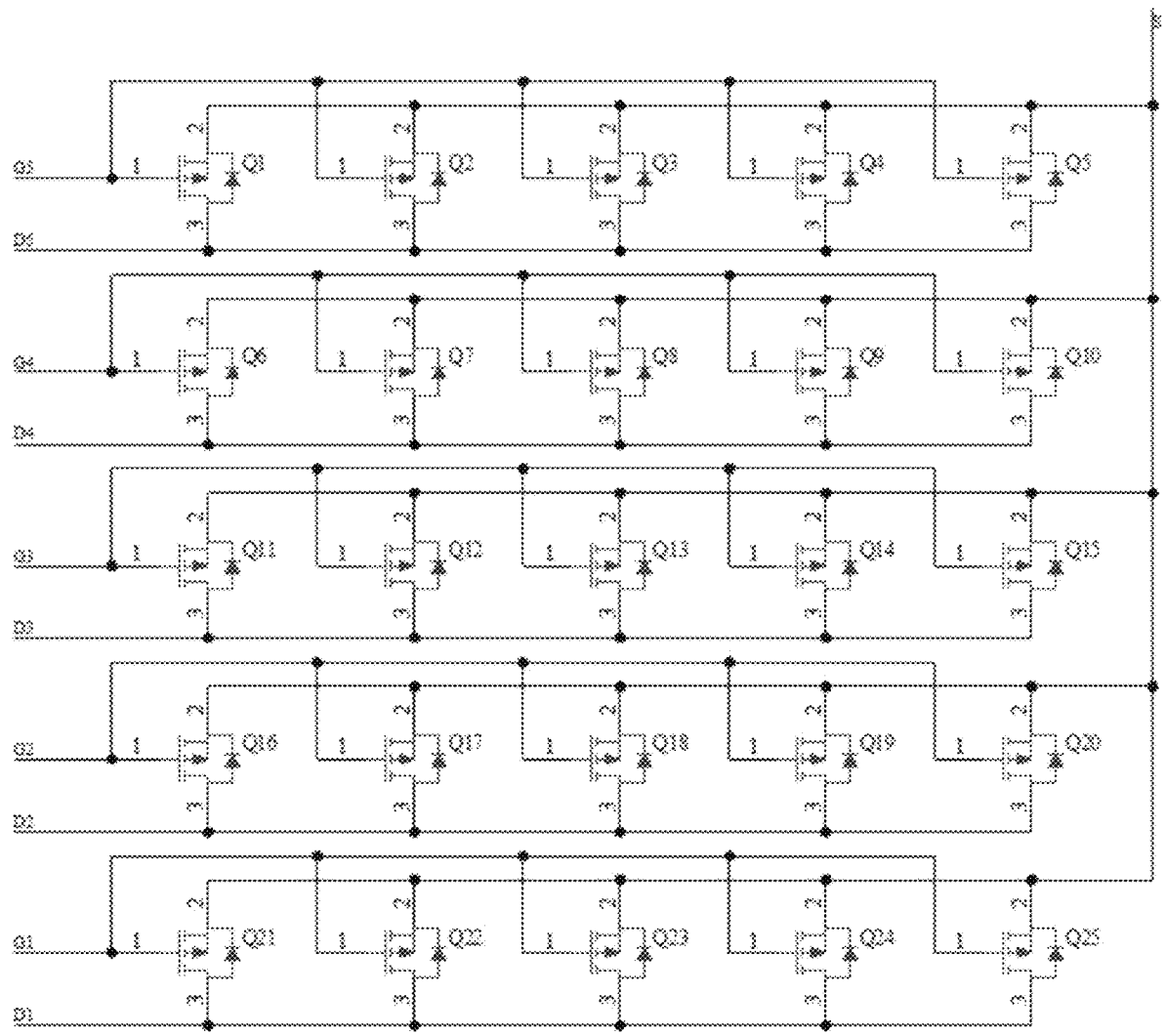
FIG. 1 is a schematic diagram of a 5×5 gas-sensitive OFET array of the present disclosure.

Technical solutions in examples of the present disclosure are described clearly and completely in the following with reference to the attached drawings in the examples of the present disclosure. Obviously, all the described examples are only some, rather than all examples of the present disclosure. Based on the examples in the present disclosure, all other examples obtained by those of ordinary skill in the art without creative efforts belong to the scope of protection of the present disclosure.

The present disclosure provides a drain-gate voltage excitation and source-drain current acquisition system for gas-sensitive OFETs, including an acquisition device and a gas-sensitive OFET array. The device includes a microcontroller module, a power supply management module, a voltage excitation module, a voltage regulation module, a TIA module, a fully-differential low-side current detection module, a voltage acquisition module, a signal transmission module and an array switching module. Through the device, the excitation of drain voltages and gate voltages in the gas-sensitive OFETs and the acquisition of source-drain currents are realized, and the performance testing of the gas-sensitive OFETs and the long-term efficient and stable monitoring of external harmful gases are finally realized through data analysis.

The microcontroller module is configured to realize the information interaction with a voltage excitation module, a voltage detection module and a signal transmission module and control an array switching module using an STM32F103C8T6 chip, mainly functioning through SPI communication, IIC communication, serial communication and level output of 10 port of the chip. In the power supply management module, a TPS7A5301 chip is adopted to realize the conversion from 3.7 V input to 3.3 V output of a lithium battery, providing a stable and suitable working voltage for the microcontroller module, the signal transmission module and the array switching module; an LTC3245 chip is adopted to realize an output of a lithium battery from 3.7 V up to 5 V, supplying power for the voltage excitation module, the voltage acquisition module and the TIA module, and providing positive power supply support for the voltage regulation module and the fully-differential low-side current detection module; and an LTC1983 chip is adopted to realize an output from 5 V to −5 V, providing negative power supply support for the voltage regulation module and the fully-differential low-side current detection module. In the voltage excitation module, a 16-bit DAC8562 chip is adopted; and one of double channels of output voltages is outputted to the gate electrode via the voltage regulation module, and the other of the double channels of output voltages is outputted to the drain electrode via the voltage regulation module to complete the independent excitation of gate and drain electrodes. The voltage regulation module is constructed from a 6-channel amplifier including a four-channel precision operational amplifier AD8674 and a two-channel precision operational amplifier AD8672, mainly performing inverting and noninverting double gain amplification and following on voltages directly outputted by the voltage excitation module, and outputting the voltages to the gate and drain electrodes. It is ensured that excitation voltages on two electrodes range from −5 V to 0 V, output currents being in mA level, and the mismatching of output currents caused by different performance of the gas-sensitive OFETs is prevented. The TIA module is configured to include a JFET-type single channel operational amplifier ADA4622 and have a bias current in pA level, reducing a baseline current to a maximum extent; and a 1 MΩ precision resistor with a precision of 0.1% is used for a feedback resistor in the module. The fully-differential low-side current detection module is configured to construct a one-stage fully-differential amplification circuit with a gain of 10 using an LT6370 instrumentation amplifier, and construct a two-stage amplification circuit with a gain of 500 using OPA4134, a total gain being 5000. The voltage acquisition module, constructed by a 16-bit ADS1115 chip, is configured to have four input channels for detecting a gate voltage, a drain voltage, an output voltage of the TIA module and an output voltage of the fully-differential low-side current detection module to realize the closed-loop control of the gate and drain voltages and simultaneously detect output voltages of two current detection modules. The signal transmission module, using an ESP32 chip, is configured to switch BLE and LAN at any time to adapt to the wireless data transmission in various environments. The array switching module is configured to use ADG series analog switches with low conduction internal resistance, the switch being capable of switching one of multiple inputs to a common output, to realize the fast switching scanning of an array.

The gas-sensitive OFET array can be set for detecting five external harmful gases of carbon dioxide, sulfur dioxide, nitrogen dioxide, carbon monoxide and ammonia, as shown in FIG. 1, Q1-Q25 are gas-sensitive OFETs, forming a 5*5 array; the array shares a source electrode; and each row of the array shares a grid electrode and a drain electrode. Therefore, a total of 11 electrodes cooperate, including 5 drain electrodes D1\D2\D3\D4\D5, 5 grid electrodes G1\G2\G3\G4\G5 and one source electrode S. Each row in the array detects one gas while each row of gas-sensitive OFETs works, and carbon dioxide, sulfur dioxide, nitrogen dioxide, carbon monoxide and ammonia are detected from bottom to top in FIG. 1. The cooperation with the array switching module can realize the rapid switching among rows of the array. Moreover, since there are two current detection circuits, the total gate leakage current caused by a common source and common grids can be filtered out from drain-source currents.

Figure 2:
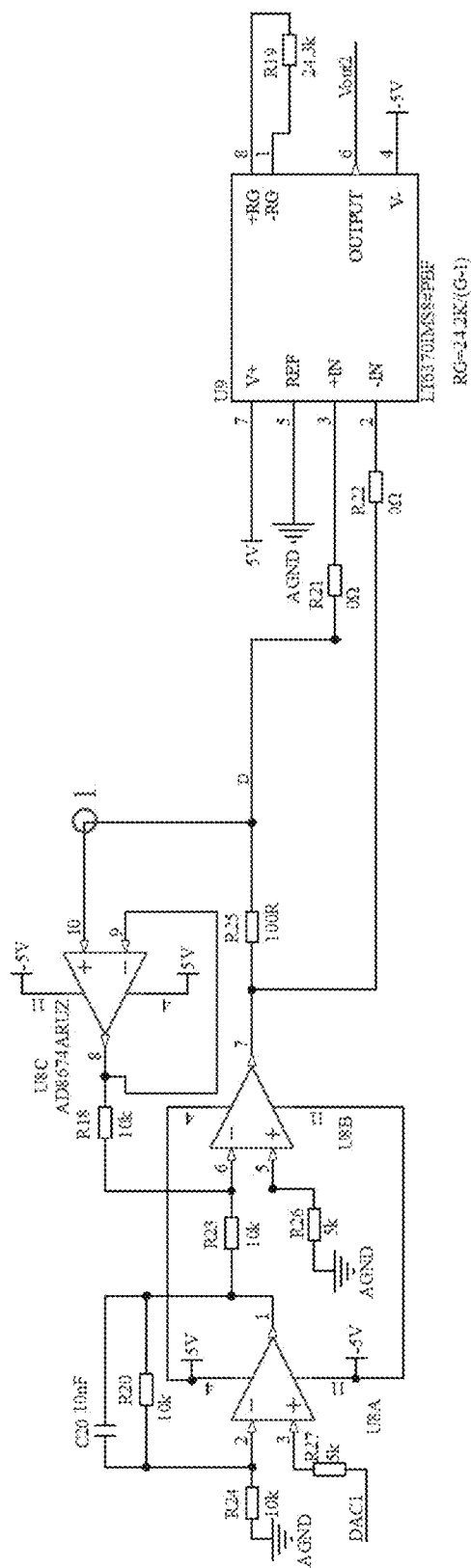
FIG. 2 is a schematic circuit diagram of a negative feedback loop having an extremely high input impedance of the present disclosure.

A fully-differential low-side current detection method is further provided, and a circuit is shown in FIG. 2. A current is converted to a voltage using a precision sampling resistor, a voltage drop of the precision sampling resistor is amplified using an LT6370 instrumentation amplifier, and a feedback loop is constructed by using the characteristic of a very high input impedance of an operational amplifier, so that drain-source currents of gas-sensitive OFETs pass through the precision sampling resistor to form a voltage negative feedback circuit without drawing currents from the gas-sensitive OFETs (as shown by a node 1 in FIG. 2, here is a noninverting input end of the amplifier, and no current passes through), thereby not only stabilizing drain electric potentials and enabling the drain electric potentials to be well controlled, but also enabling the drain-source currents to be measured with sufficient accuracy. The method requires attention to that: the precision sampling resistor is equivalent to the output resistance of the operational amplifier in the circuit. According to the criterion that the output impedance of a previous stage circuit is to be smaller, the value of the precision sampling resistor is not to be too large. However, since it is not sensitive to a change response of a current when a resistance value is too small, a precision resistor with a resistance value of 100Ω is selected and needs to be calibrated before use.

Figure 3:
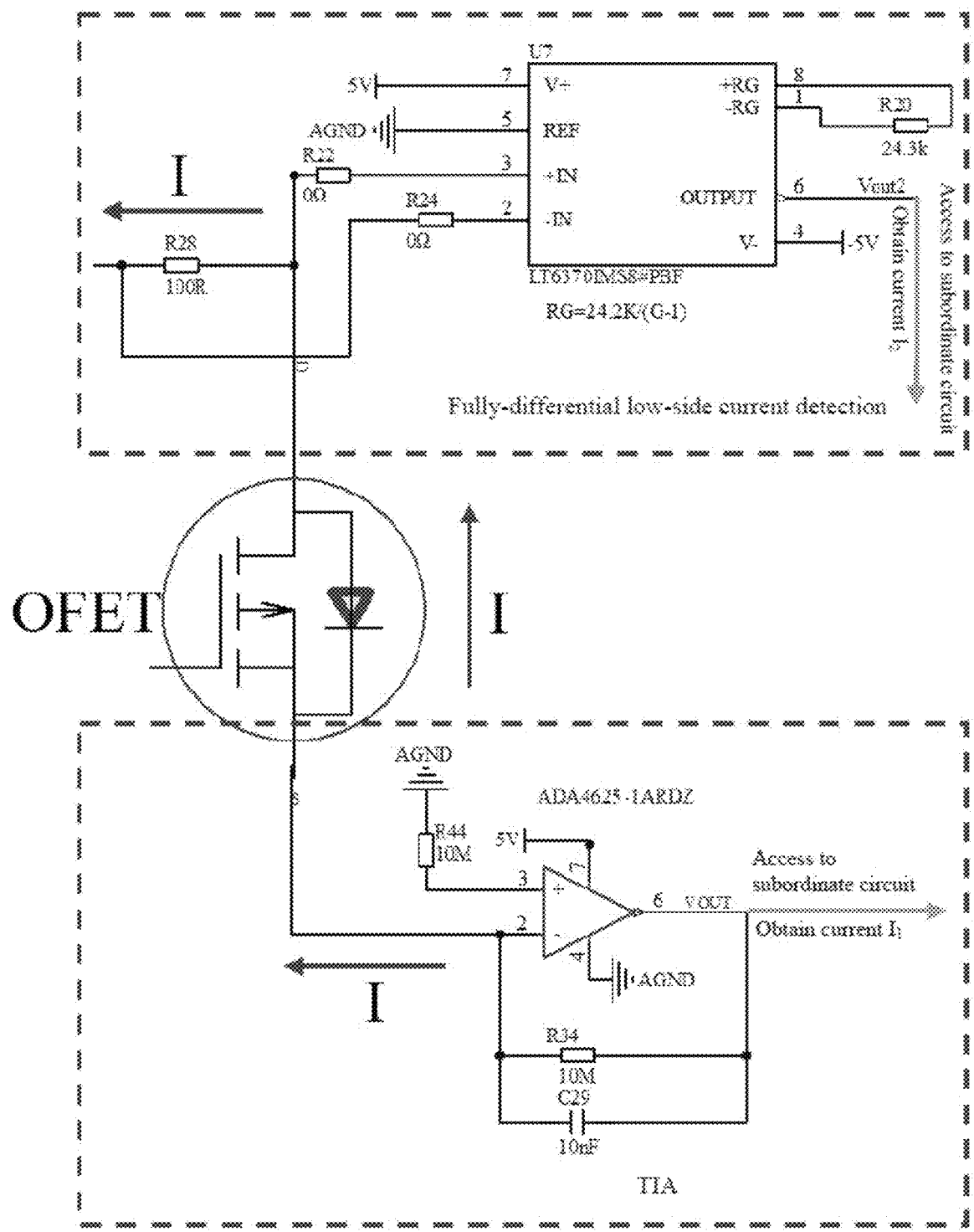
FIG. 3 is a schematic circuit diagram of two current detection methods of the present disclosure.

A method for implementing detection of different orders of currents with higher accuracy using a weighted mode is further provided, including the steps that: two current detection methods are adopted, as shown in FIG. 3, namely TIA and fully-differential low-side current detection; a weighted sum of results of currents acquired by the two methods is taken as a final result of a current transmitted to a terminal; and different weights are added to the two current detection results according to different orders of drain-source currents, followed by summing. For example: a TIA result is $I_1$, a fully-differential low-side current detection result is $I_2$, and a final result of a current transmitted to a terminal is I, then $I=\alpha I_1+(1-\alpha)I_2$, where $0\leq\alpha\leq1$. When a drain-source current is in nA level, α is taken to be large; and when a drain-source current is in μA level, α is taken to be small, effectively preventing the overflow of the TIA circuit due to excessive currents.

A wireless terminal for drain/gate voltage excitation and source-drain current acquisition for gas-sensitive OFETs is provided for implementing the control of a drain-gate voltage excitation and source-drain current acquisition device for gas-sensitive OFETs, and the wireless transmission, storage and intelligent analysis of detection data through a system wireless terminal by connecting a Wi-Fi signal or a BLE signal sent by a signal transmission module and using three communication modes, data coding at a signal sending end and data parsing at the wireless terminal, to realize the sensitive analysis and timely alarm of various harmful gases.

The wireless terminal is mainly divided into three interfaces.

A communication mode selection part is included. An information display area including information such as air quality, geographical location and air temperature is arranged at an upper part of the home page, and three communication mode selection buttons of BLE, Internet of Things (IoT) and user datagram protocol (UDP) are arranged at a lower part. When a BLE button is clicked, a BLE equipment list secondary interface is transferred, and a user can select the corresponding equipment for connection. The communication modes of BLE and UDP are that the wireless terminal and the drain/gate voltage excitation and source-drain current acquisition device for gas-sensitive OFETs can be connected successfully within a certain distance, and the communication mode of IoT uses the communication technology of IoT. Therefore, it is required that the wireless terminal and the drain/gate voltage excitation and source-drain current acquisition device for gas-sensitive OFETs must be connected to an available LAN. However, but the two are no longer required to be within a certain distance, and the communication mode can realize the remote control.

A parameter selection part is included. An introduction column of harmful gases to be monitored is arranged, including the introduction of physical and chemical properties of and preventive measures on harmful gases. A selection button for detecting five harmful gases is arranged at a lower part of this interface, the analysis of the harmful gas can be immediately performed by clicking a corresponding button, and a final concentration of the harmful gas is displayed in an area of the corresponding button.

A drawing part is included. A drawing coordinate area and three buttons of drawing, clearing and saving are arranged, and this interface provides a visual interface for a user. The drawing button is clicked to parse data sent by the device and draw a curve in the drawing coordinate area in real time; the clearing button is clicked to erase the curve in the coordinate area; and the saving button is clicked to save the parsed data for subsequent analysis by the user.

The last points that are to be explained are as follows. Firstly, in the description of the present application, unless otherwise specified and limited, it is to be understood that the terms "mounted", "linked" and "connected" are to be understood in a broad sense, for example, "connected" may be mechanically connected, electrically connected, an internal communication between two elements, or directly connected; and "upper", "lower", "left", "right", and the like are used merely to indicate relative positional relationships that may change when an absolute position of an object being described changes.

Secondly, in the drawings of the disclosed examples of the present disclosure, only the structures related to the disclosed examples are involved, and other structures can refer to the usual designs, and the same example and different examples of the present disclosure can be combined without conflict.

Finally: the above is only the preferred examples of the present disclosure, which are not used to limit the present disclosure. Any modifications, equivalent substitutions and improvements made within the spirit and principle of the present disclosure are to be included in the scope of protection of the present disclosure.

The invention claimed is:

1. A drain-gate voltage excitation and source-drain current acquisition system for gas-sensitive organic field effect transistors (OFETs), comprising an acquisition device and a gas-sensitive OFET array, the device comprising:
   a microcontroller module, configured to realize the information interaction with a voltage excitation module, a voltage detection module and a signal transmission module and control an array switching module;
   a power supply management module;
   the voltage excitation module, configured to complete the independent excitation of gate and drain electrodes;
   a voltage regulation module, configured to perform inverting and noninverting double gain amplification and following on voltages directly outputted by the voltage excitation module, and output the voltages to the gate and drain electrodes, ensuring that excitation voltages on two electrodes range from −5 V to 0 V, output currents being in mA level;
   a transimpedance amplifier (TIA) module, configured to have a bias current in pA level, reducing a baseline current to a maximum extent;
   a fully-differential low-side current detection module, configured to construct a one-stage fully-differential amplification circuit with a gain of 10, and construct a two-stage amplification circuit with a gain of 500, a total gain being 5000;
   a voltage acquisition module, configured to have four input channels for detecting a gate voltage, a drain voltage, an output voltage of the TIA module and an output voltage of the fully-differential low-side current detection module;
   the signal transmission module, configured to switch Bluetooth low energy (BLE) and local area network (LAN) at any time; and
   the array switching module, configured to use ADG series analog switches with low conduction internal resistance to realize the fast switching scanning of the array;
   a size of the gas-sensitive OFET array being 5*5, each row in the array detecting a gas, the array sharing one source electrode, and each row of the array sharing one gate electrode and one drain electrode to realize the fast switching among rows of the array.

2. The drain-gate voltage excitation and source-drain current acquisition system for gas-sensitive OFETs according to claim 1, wherein in the microcontroller module, an STM32F103C8T6 chip is adopted, functioning through serial peripheral interface (SPI) communication, inter-integrated circuit (IIC) communication, serial communication and level output of input/output (IO) port of the chip; and
   in the power supply management module, a TPS7A5301 chip is adopted to realize the conversion from 3.7 V input to 3.3 V output of a lithium battery, providing a stable and suitable working voltage for the microcontroller module, the signal transmission module and the array switching module; an LTC3245 chip is adopted to realize an output of a lithium battery from 3.7 V up to 5 V, supplying power for the voltage excitation module, the voltage acquisition module and the TIA module, and providing positive power supply support for the voltage regulation module and the fully-differential low-side current detection module; and an LTC1983 chip is adopted to realize an output from 5 V to −5 V, providing negative power supply support for the voltage regulation module and the fully-differential low-side current detection module.

3. The drain-gate voltage excitation and source-drain current acquisition system for gas-sensitive OFETs according to claim 1, wherein in the voltage excitation module, a 16-bit DAC8562 chip is adopted; and one of double channels of output voltages is outputted to the gate electrode via the voltage regulation module, and the other of the double channels of output voltages is outputted to the drain electrode via the voltage regulation module; and the voltage regulation module is constructed from a 6-channel amplifier comprising a four-channel precision operational amplifier AD8674 and a two-channel precision operational amplifier AD8672.

4. A fully-differential low-side current detection method using a drain-gate voltage excitation and source-drain current acquisition system for gas-sensitive OFETs according to claim 1, comprising the steps of: converting a current to a voltage using a precision sampling resistor, and amplifying a voltage drop of the precision sampling resistor using an LT6370 instrumentation amplifier to cause a drain electric potential to be well controlled and a drain-source current to be measured with sufficient accuracy.

5. A fully-differential low-side current detection method using a drain-gate voltage excitation and source-drain current acquisition system for gas-sensitive OFETs according to claim 2, comprising the steps of: converting a current to a voltage using a precision sampling resistor, and amplifying a voltage drop of the precision sampling resistor using an LT6370 instrumentation amplifier to cause a drain electric potential to be well controlled and a drain-source current to be measured with sufficient accuracy.

6. A fully-differential low-side current detection method using a drain-gate voltage excitation and source-drain current acquisition system for gas-sensitive OFETs according to claim 3, comprising the steps of: converting a current to a voltage using a precision sampling resistor, and amplifying a voltage drop of the precision sampling resistor using an LT6370 instrumentation amplifier to cause a drain electric potential to be well controlled and a drain-source current to be measured with sufficient accuracy.

7. A method for implementing detection of different orders of currents with higher accuracy using a weighted mode for a drain-gate voltage excitation and source-drain current acquisition system for gas-sensitive OFETs according to claim 1, comprising the steps of: adopting two current detection methods, namely TIA and fully-differential low-side current detection; taking a weighted sum of results of currents acquired by the two methods as a final result of a current transmitted to a terminal; and adding different weights to the two current detection results according to different orders of drain-source currents, followed by summing.

8. A method for implementing detection of different orders of currents with higher accuracy using a weighted mode for a drain-gate voltage excitation and source-drain current acquisition system for gas-sensitive OFETs according to claim 2, comprising the steps of: adopting two current detection methods, namely TIA and fully-differential low-side current detection; taking a weighted sum of results of currents acquired by the two methods as a final result of a current transmitted to a terminal; and adding different weights to the two current detection results according to different orders of drain-source currents, followed by summing.

9. A method for implementing detection of different orders of currents with higher accuracy using a weighted mode for a drain-gate voltage excitation and source-drain current acquisition system for gas-sensitive OFETs according to claim 3, comprising the steps of: adopting two current detection methods, namely TIA and fully-differential low-side current detection; taking a weighted sum of results of currents acquired by the two methods as a final result of a current transmitted to a terminal; and adding different weights to the two current detection results according to different orders of drain-source currents, followed by summing.

10. A wireless terminal using a drain-gate voltage excitation and source-drain current acquisition system for gas-sensitive OFETs according to claim 1 for implementing the control of a drain-gate voltage excitation and source-drain current acquisition device for gas-sensitive OFETs, and the wireless transmission, storage and intelligent analysis of detection data through a system wireless terminal by connecting a wireless fidelity (Wi-Fi) signal or a BLE signal sent by a signal transmission module and using three communication modes, data coding at a signal sending end and data parsing at the wireless terminal, to realize the sensitive analysis and timely alarm of various harmful gases.

11. A wireless terminal using a drain-gate voltage excitation and source-drain current acquisition system for gas-sensitive OFETs according to claim 2 for implementing the control of a drain-gate voltage excitation and source-drain current acquisition device for gas-sensitive OFETs, and the wireless transmission, storage and intelligent analysis of detection data through a system wireless terminal by connecting a wireless fidelity (Wi-Fi) signal or a BLE signal sent by a signal transmission module and using three communication modes, data coding at a signal sending end and data parsing at the wireless terminal, to realize the sensitive analysis and timely alarm of various harmful gases.

12. A wireless terminal using a drain-gate voltage excitation and source-drain current acquisition system for gas-sensitive OFETs according to claim 3 for implementing the control of a drain-gate voltage excitation and source-drain current acquisition device for gas-sensitive OFETs, and the wireless transmission, storage and intelligent analysis of detection data through a system wireless terminal by connecting a wireless fidelity (Wi-Fi) signal or a BLE signal sent by a signal transmission module and using three communication modes, data coding at a signal sending end and data parsing at the wireless terminal, to realize the sensitive analysis and timely alarm of various harmful gases.

\* \* \* \* \*